United States Patent
Kim et al.

(10) Patent No.: US 11,104,636 B2
(45) Date of Patent: Aug. 31, 2021

(54) SYSTEM AND METHOD FOR MANUFACTURING ESTER-BASED COMPOSITION

(71) Applicant: LG CHEM, LTD., Seoul (KR)

(72) Inventors: Hyun Kyu Kim, Daejeon (KR); Sung Kyu Lee, Daejeon (KR); Hyoung Jun, Daejeon (KR); Chan Hyu Jin, Daejeon (KR); Jeong Ju Moon, Daejeon (KR); Joo Ho Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 16/838,279

(22) Filed: Apr. 2, 2020

(65) Prior Publication Data

US 2020/0317599 A1    Oct. 8, 2020

(30) Foreign Application Priority Data

Apr. 4, 2019 (KR) .................. 10-2019-0039715
Mar. 30, 2020 (KR) .................. 10-2020-0038457

(51) Int. Cl.
| | | |
|---|---|---|
| *B01J 19/00* | (2006.01) | |
| *C07C 67/02* | (2006.01) | |
| *C07C 67/08* | (2006.01) | |
| *C07C 67/58* | (2006.01) | |
| *B01J 4/00* | (2006.01) | |

(Continued)

(52) U.S. Cl.
CPC .............. *C07C 67/08* (2013.01); *B01D 3/14* (2013.01); *B01J 4/008* (2013.01); *B01J 8/04* (2013.01); *B01J 19/0013* (2013.01); *B01J 19/0046* (2013.01); *B01J 19/0053* (2013.01); *C07C 67/02* (2013.01); *C07C 67/58* (2013.01); *B01J 2219/0004* (2013.01); *B01J 2219/00038* (2013.01); *B01J 2219/00051* (2013.01);

(Continued)

(58) Field of Classification Search
None
See application file for complete search history.

(56) References Cited

U.S. PATENT DOCUMENTS 2,644,009 A * 6/1953 Cash .................. C07C 67/08
                                                    560/98
4,241,216 A * 12/1980 Bergman ............. C07C 67/08
                                                    560/191

(Continued)

FOREIGN PATENT DOCUMENTS

| JP | 2005-350630 A | 12/2005 |
|---|---|---|
| JP | 2010-095467 A | 4/2010 |

(Continued)

OTHER PUBLICATIONS

Janjua.(2007).Systemic Uptake of Diethyl Phthalate, Dibutyl Phthalate, and Butyl Paraben Following Whole-Body Topical Application and Reproductive and Thyroid Hormone Levels in Humans. Environ. Sci. Technol. vol. 14, pp. 5564-5570.

(Continued)

*Primary Examiner* — Jennifer A Leung
(74) *Attorney, Agent, or Firm* — Dentons US LLP

(57) ABSTRACT

The present disclosure relates to a manufacturing system and a manufacturing method which are capable of continuously manufacturing an ester-based composition, and has a technical feature of being capable of manufacturing an ether-based composition continuously, economically, and efficiently.

9 Claims, 3 Drawing Sheets

(51) Int. Cl.
*B01D 3/14* (2006.01)
*B01J 8/04* (2006.01)
*C07C 67/54* (2006.01)

(52) U.S. Cl.
CPC .............. *B01J 2219/00159* (2013.01); *B01J 2219/00186* (2013.01)

(56) References Cited

U.S. PATENT DOCUMENTS

| | | | | |
|---|---|---|---|---|
| 7,700,793 | B2* | 4/2010 | Iyer | C11C 3/04 554/174 |
| 8,410,306 | B2* | 4/2013 | Bauduin | C07C 67/08 560/190 |
| 2007/0277430 | A1* | 12/2007 | Jackman | C11C 3/003 44/308 |
| 2009/0099380 | A1 | 4/2009 | Aiken | |
| 2010/0130767 | A1* | 5/2010 | De Munck | C07C 67/08 560/99 |
| 2010/0242346 | A1* | 9/2010 | Bunning | C11C 3/003 44/388 |
| 2019/0263745 | A1 | 8/2019 | Lee et al. | |

FOREIGN PATENT DOCUMENTS

| | | |
|---|---|---|
| KR | 10-2013-0042742 A | 4/2013 |
| KR | 10-1354141 B1 | 1/2014 |
| KR | 10-1663586 B1 | 10/2016 |
| KR | 10-2019-0027623 A | 3/2019 |
| WO | 2007/074750 A1 | 7/2007 |

OTHER PUBLICATIONS

Rahman, (2004).The Plasticizer Market: an Assessment of Traditional Plasticizers and Research Trends to Meet New Challenges. Prog. Polym. Sci. vol. 29. pp. 1223-1248.

* cited by examiner

SYSTEM AND METHOD FOR MANUFACTURING ESTER-BASED COMPOSITION

CROSS-REFERENCE TO RELATED APPLICATIONS

This application claims the benefit of and priority to Korean Application No. 10-2019-0039715, filed on Apr. 4, 2019 and Korean Application No. 10-2020-0038457, filed on Mar. 30, 2020, all of which are incorporated by reference in their entirety for all purpose as if fully set forth herein.

TECHNICAL FIELD

The present invention relates to a method and a system for manufacturing an ester-based composition efficiently and continuously.

BACKGROUND ART

Phthalate-based plasticizers had occupied 92% of the world's plasticizer market by the 20th century (Mustafizur Rahman and Christopher S. Brazel "The plasticizer market: an assessment of traditional plasticizers and research trends to meet new challenges" Progress in Polymer Science 2004, 29, 1223-1248), and are additives used to improve the processability of polyvinyl chloride (hereinafter, referred to as PVC) by imparting flexibility, durability, cold resistance, and the like and lowering viscosity during melting. Phthalate-based plasticizers are introduced into PVC in various contents and used not only for hard products such as rigid pipes, but also for soft products such as food packaging materials, blood bags, and flooring materials since the phthalate-based plasticizers are soft and stretchable. Thus, the phthalate-based plasticizers are more closely related to real life than any other materials and are widely used for materials which come into direct contact with a human body.

However, despite the compatibility with PVC and excellent softness imparting properties of phthalate-based plasticizers, there has been controversy over the harmful nature of the phthalate-based plasticizers in that when a PVC product containing a phthalate-based plasticizer is used in real life, the phthalate-based plasticizer may be leaked little by little out of the product and act as a suspected endocrine disruptor (environmental hormone) and a carcinogen to the level of a heavy metal (N R Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2007, 41, 5564-5570). Particularly, since a report was published in the 1960s in the United States that diethylhexyl phthalate (di-(2-ethylhexyl) phthalate, DEHP), the most used phthalate plasticizer, leaked out of PVC products, global environmental regulations have started to be implemented in addition to various studies on the harmful nature of the phthalate-based plasticizer on human bodies, boosted by increasing interest in environmental hormones in the 1990s.

Thus, in order to respond to environmental hormonal problems and environmental regulations due to the leakage of phthalate-based plasticizers, many researchers have been conducting research in order to develop a new non-phthalate-based alternative plasticizer without phthalic anhydride used in the manufacturing of phthalate-based plasticizers, or to develop a leakage suppression technology which suppresses the leakage of phthalate-based plasticizers, thereby significantly reducing risks to human bodies and which meets environmental standards.

Meanwhile, as non-phthalate-based plasticizers, terephthalate-based plasticizers not only have an equivalent level of physical properties with phthalate-based plasticizers, but also have been spotlighted as a material free from environmental problems, so that various types of terephthalate-based plasticizers have been developed. In addition, research on developing terephthalate-based plasticizers with excellent physical properties as well as research on equipment for manufacturing such terephthalate-based plasticizers have been actively conducted, and there has been a demand for more efficient, more economical and simpler process designs in terms of process design.

PRIOR ART DOCUMENT (Patent Document 1) Korean Patent Laid-Open Publication No. 10-1354141

(Non-patent Document 1) Mustafizur Rahman and Christopher S. Brazel "The plasticizer market: an assessment of traditional plasticizers and research trends to meet new challenges" Progress in Polymer Science 2004, 29, 1223-1248

(Non-patent Document 2) N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2007, 41, 5564-5570

DISCLOSURE OF THE INVENTION

Technical Problem

An aspect of the present invention provides a manufacturing system and a manufacturing method for continuously manufacturing an ester-based composition efficiently and economically.

Technical Solution

According to an aspect of the present invention, there is provided a system for manufacturing an ester-based composition, the system including a mixing unit in which a reaction mixture of a polycarboxylic acid and a first alcohol is formed, a reaction unit in which an esterification reaction of the reaction mixture is performed to form a first unpurified product mixture including a first ester compound, a trans-reaction unit in which a trans-esterification reaction of the first unpurified product mixture formed in the reaction unit and a second alcohol separately injected is performed to form a second unpurified product mixture including a second ester compound, a neutralization unit in which the neutralization and water separation of the second unpurified product mixture are performed to form a water layer stream and an organic layer stream, a distillation unit in which an alcohol-rich stream and an ester-rich stream are formed by distilling the organic layer stream, and a product purifying unit for removing the first alcohol and the second alcohol remaining in the ester-rich stream to form a mixed alcohol stream and a product stream including the first alcohol and the second alcohol.

According to another aspect of the present invention, there is provided a method for manufacturing an ester-based composition, the method performed through the above-described manufacturing system and including, specifically, S1 of forming a reaction mixture of a polycarboxylic acid and a first alcohol, S2 of performing an esterification reaction of the reaction mixture to form a first unpurified product mixture including a first ester compound, S3 of performing a trans-esterification reaction of the first unpurified product mixture and a second alcohol to form a second unpurified product mixture including a second ester compound, S4 of performing the neutralization and water separation of the second unpurified product mixture to form a water layer stream and an organic layer stream, S5 of distilling the organic layer stream to obtain an alcohol-rich stream and an ester-rich stream, and S6 of removing the first alcohol and the second alcohol remaining in the ester-rich stream to obtain a mixed alcohol stream and a product stream.

Advantageous Effects

When a manufacturing system of the present invention is used, an entire manufacturing process may be continuously operated, so that an ester-based composition may be manufactured efficiently and economically, and the amount of energy used during the process or the amount of wastewater discharged as a by-product of the manufacturing process is reduced, so that an ester-based composition may be manufactured in an environment-friendly manner.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

MODE FOR CARRYING OUT THE INVENTION

Figure 1:
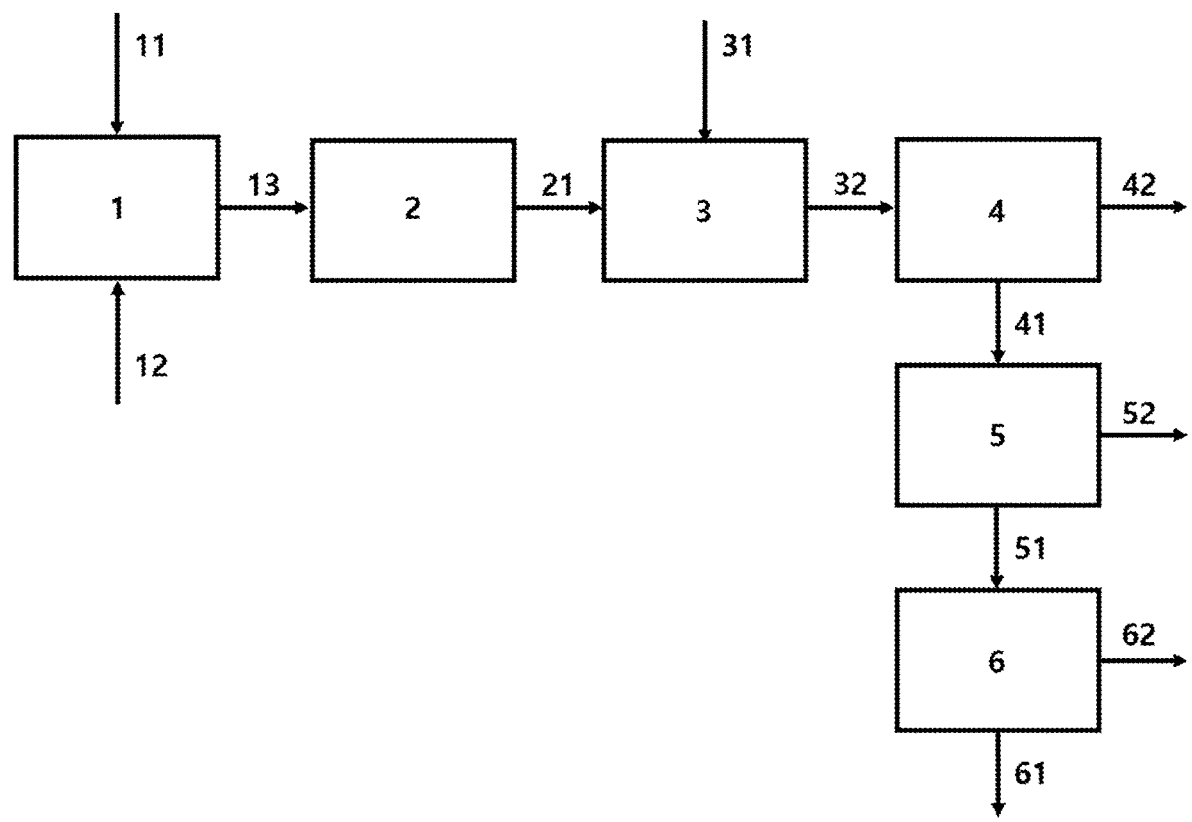
FIG. 1 is a schematic diagram illustrating a system for manufacturing an ester-based composition of the present invention, the system including a mixing unit, a reaction unit, a trans-reaction unit, a neutralization unit, a distillation unit, and a product purifying unit.

Hereinafter, the present invention will be described in more detail.

It will be understood that words or terms used in the specification and claims of the present invention shall not be construed as being limited to having the meaning defined in commonly used dictionaries. It will be further understood that the words or terms should be interpreted as having meanings that are consistent with their meanings in the context of the relevant art and the technical idea of the invention, based on the principle that an inventor may properly define the meaning of the words or terms to best explain the invention.

In the manufacturing method and the manufacturing system of the present invention, a polycarboxylic acid refers to a compound having two or more carboxylic acid groups, for example, a dicarboxylic acid, a tricarboxylic acid, or a tetracarboxylic acid. A polycarboxylic acid used in the present invention may have 2 to 5 carboxylic acid groups, 2 to 4 carboxylic acid groups, or 2 to 3 carboxylic acid groups. When a polycarboxylic acid has too many carboxylic acid groups, it may not easy to apply the polycarboxylic acid to the manufacturing method or the manufacturing system of the present invention due to a high molecular weight of the polycarboxylic acid itself. The polycarboxylic acid is preferably a dicarboxylic acid, a tricarboxylic acid, or a tetracarboxylic acid. The dicarboxylic acid may be one or more selected from the group consisting of a linear dicarboxylic acid having 2 to 10 carbon atoms, a terephthalic acid, a phthalic acid, an isophthalic acid, and a cyclohexane dicarboxylic acid, and the tricarboxylic acid may be one or more selected from the group consisting of a citric acid, a trimellitate acid, and a cyclohexane tricarboxylic acid. The tetracarboxylic acid may be one or more selected from the group consisting of a benzenetetracarboxylic acid, a furantetracarboxylic acid, a cyclohexane tetracarboxylic acid, and a tetrahydrofuran tetracarboxylic acid. In addition, the polycarboxylic acid may not only include itself, but also include an anhydride or a derivative thereof.

In the manufacturing method and the manufacturing system of the present invention, each of a first alcohol and a second alcohol is alcohol having 3 to 10 alkyl carbon atoms, and the first alcohol and the second alcohol have different numbers of alkyl carbon atoms. The alcohol having 3 to 10 alkyl carbon atoms may be one or more selected from the group consisting of propanol, butanol, pentanol, hexanol, heptanol, octanol, nonanol and decanol, all of which are of a linear-type or a branched-type. In addition, each of the first alcohol and the second alcohol may be alcohol of a single type, or may be in the form of a mixture containing isomers having the same number of carbon atoms. For example, when the first alcohol is alcohol having 3 alkyl carbon atoms, the first alcohol may be one of 1-propanol or 2-propanol, or may be in the form of a mixture containing 1-propanol and 2-propanol in a predetermined ratio. When the first alcohol and the second alcohol are in the form of a mixture containing isomers having the same number of carbon number, the relative amount of each isomer is not particularly limited.

In addition, in the manufacturing method and the manufacturing system of the present invention, lower alcohol and higher alcohol respectively refer to alcohol having the smaller number of carbon atoms and alcohol having the larger number of carbon atoms between the first alcohol and the second alcohol used in the present invention. For example, if propanol is used as the first alcohol and nonanol is used as the second alcohol, the lower alcohol refers to propanol which is the first alcohol, and the higher alcohol refers to nonanol which is the second alcohol. If hexanol is used as the first alcohol and butanol is used as the second alcohol, the lower alcohol refers to butanol which is the second alcohol and the higher alcohol refers to hexanol which is the first alcohol.

In the manufacturing method and the manufacturing system of the present invention, a first ester compound refers to an ester compound formed by an esterification reaction between a first alcohol and a polycarboxylic acid. Specifically, the first ester compound is an ester bond formed by a reaction between at least one of a plurality of carboxylic acid groups contained in a polycarboxylic acid and a first alcohol, and more specifically, an ester bond formed by a reaction between one, two, or more of carboxylic acid groups contained in the polycarboxylic acid with the first alcohol.

In the manufacturing method and the manufacturing system of the present invention, a second ester compound refers to an ester compound formed by a trans-esterification reaction of a second alcohol and the first ester compound. Specifically, the second ester compound is formed by a trans-esterification reaction between at least one of a plurality of ester groups included in the first ester compound and the second alcohol, and more specifically, formed by a trans-esterification reaction between one, two, or more of ester groups contained in the first ester compound and the second alcohol.

An "upper portion" of equipment described in the present specification to describe the manufacturing system, the equipment being, for example, a column, a distiller, a neutralizer, a wastewater treatment tank, or the like, may include, unless specifically specified, the top surface of each piece of equipment, thereby including a side top surface located above the center in the height direction of a side surface, and an "lower portion" of the equipment may include, unless specifically specified, the bottom surface of each piece of the equipment, thereby including a side bottom surface located below the center in the height direction of the side surface.

In the manufacturing method and the manufacturing system of the present invention, a stream means a flow of a fluid moving from one component constituting the system to another component in the system or outside the system, and the fluid includes both gas and liquid.

The system for manufacturing an ester-based composition of the present invention may be continuously operated. As to be described later, all components constituting the manufacturing system of the present invention may be continuously operated, and thus, the manufacturing system may be continuously operated. Therefore, when the manufacturing system of the present invention is used, there is an advantage in that it is possible to uniformly and efficiently manufacture an ester-based composition, which is the final product. In the present invention, "continuous" means that each component or step may be operated or performed simultaneously.

System for manufacturing ester-based composition

An aspect of the present invention provides a system for manufacturing an ester-based composition, the system including a mixing unit in which a reaction mixture of a polycarboxylic acid and a first alcohol is formed, a reaction unit in which an esterification reaction of the reaction mixture is performed to form a first unpurified product mixture including a first ester compound, a trans-reaction unit in which a trans-esterification reaction of the first unpurified product mixture formed in the reaction unit and a second alcohol separately injected is performed to form a second unpurified product mixture including a second ester compound, a neutralization unit in which the neutralization and water separation of the second unpurified product mixture are performed to form a water layer stream and an organic layer stream, a distillation unit in which an alcohol-rich stream and an ester-rich stream are formed by distilling the organic layer stream, and a product purifying unit for removing the first alcohol and the second alcohol remaining in the ester-rich stream to form a mixed alcohol stream and a product stream including the first alcohol and the second alcohol.

As illustrated in FIG. 1, the system for manufacturing an ester-based composition of the present invention is composed of a mixing unit 1, a reaction unit 2, a trans-reaction unit 3, a neutralization unit 4, a distillation unit 5, and a product purifying unit 6. Each component constituting the system for manufacturing an ester-based composition of the present invention will be described in more detail below with reference to the drawings.

Mixing unit

In the system for manufacturing an ester-based composition of the present invention, the mixing unit 1 is a region in which the mixing of a first alcohol and a polycarboxylic acid, which correspond to reaction raw materials, is performed. A first alcohol 11 and a polycarboxylic acid 12 are injected into the mixing unit and mixed in an internal region of the mixing unit to form a reaction mixture 13.

In the system for manufacturing an ester-based composition of the present invention, an esterification reaction between the first alcohol 11 and the polycarboxylic acid 12 and a trans-esterification reaction between a first ester compound and a second alcohol are performed, and each of the reactions is facilitated in the state in which reaction raw materials are evenly mixed. Therefore, it is necessary to mix the first alcohol 11 and the polycarboxylic acid 12 evenly prior to the following esterification reaction in a reaction unit.

When reaction raw materials are not pre-mixed before being injected into a reactor, depending on a position inside the reactor, the non-uniformity of the raw materials may be greatly increased, and when stirring is performed poorly inside the reactor, some raw materials may be accumulated in particular, and thus, it may be difficult to secure uniform reaction duration. However, when reaction raw materials are pre-mixed and then injected, it is possible to obtain a substantially uniform reaction degree over the entire region of the reactor, and the reaction rate of each reactor may be maintained to be substantially uniform to secure the stability of the entire process.

In the present invention, the mixing unit is not particularly limited as long as the mixing unit is for performing the mixing of a first alcohol and a polycarboxylic acid smoothly, and may include a mixing apparatus such as a stirrer or a mixer. The mixing unit may include one mixing apparatus or a plurality of mixing apparatuses.

In the present invention, the mixing unit may further include a heating means in addition to the mixing apparatus. The esterification reaction in the reaction unit is performed at a relatively high temperature, so that if the reaction mixture is pre-heated in the mixing unit before being injected into the reaction unit, there is an advantage in that a reaction may start shortly after the injection of the reaction mixture into the reaction unit. The heating means may be a heat exchanger or a heater, but is not particularly limited as long as the heating means may heat a first alcohol, a polycarboxylic acid and/or a reaction mixture smoothly. When the mixing unit includes the above heating means, the temperature of the reaction mixture in the mixing unit may be 50-200° C., preferably 60-190° C., more preferably 70-180° C. When the temperature of the reaction mixture is too low, pre-heating the reaction mixture in the mixing unit before injecting the same into the reaction unit is less effective, so that it may be rather uneconomical. When the reaction mixture is heated to an excessively high temperature and then injected into a reactor, the vaporization or the like of the polycarboxylic acid and alcohol, which are reaction raw materials, may occur, so that a uniform reaction may not proceed or the loss of the reaction raw materials may occur.

Reaction Unit

The reaction mixture 13 formed in the mixing unit is then injected into the reaction unit, and in the reaction unit, an esterification reaction of the reaction mixture is performed to form a first unpurified product mixture.

Specifically, in the reaction unit, an esterification reaction between the polycarboxylic acid and the first alcohol, both being included in the reaction mixture, is performed. The esterification reaction is a reaction in which a carboxylic acid group and a hydroxy group form an ester bond and water. Through the reaction, at least one carboxylic acid group of the polycarboxylic acid is reacted with the first alcohol to form a first ester compound. Accordingly, the first unpurified product mixture formed in the present reaction unit includes the first ester compound.

The esterification reaction in the reaction unit may be performed under typical temperature and pressure conditions of an esterification reaction although there may be variations in conditions depending on the type of the first alcohol and the polycarboxylic acid, and may be performed in the presence of a catalyst typically used in the esterification reaction. Those skilled in the art may determine the temperature and pressure conditions of the reaction unit and the type and usage amount of the catalyst in consideration of the type and amount of the polycarboxylic acid and the first alcohol.

Meanwhile, the reaction unit may be provided with a plurality of reactors, more specifically, may be provided with (1) a plurality of reactors connected in series, or may be provided with (2) a plurality of reactors connected in parallel.

(1) When Provided With Plurality of Reactors Connected in Series

According to an embodiment of the present invention, the reaction unit includes N number of reactors in which a first reactor to an N-th reactor are connected in series and a variable control unit, wherein the variable control unit controls the temperature of each reactor and the amount of alcohol injected into each reactor such that the following Formulas 1) and 2) are satisfied, and N may be an integer of 2 or greater:

$$T_{n1-1} \leq T_{n1} \quad (1)$$

$$E_{n2-1} \geq E_{n2} \geq E_1 \quad (2)$$

in Formulas above, n1 is an integer of 2 to N, and n2 is an integer of 3 to N.

$T_x$=Temperature of an x-th reactor.

$E_x$={(Number of moles of alcohol injected into an x-th reactor−c*Number of moles of polycarboxylic acid injected into an x-th reactor/c*Number of moles of polycarboxylic acid injected into the first reactor)*100%}

In $T_x$ and $E_x$, x is an integer of 1 to N, and c is the number of carboxylic acid groups contained in one molecule of the polycarboxylic acid.

When the reaction unit is composed of a plurality of reactors connected in series, not just one reactor, process design costs may be reduced by reducing the size of each reactor, and a reaction mixture may be continuously injected into the plurality of reactors connected in series. Also, process variables may be independently controlled for each reactor to allow the optimization of the entire process. In addition, ultimately, it is possible to maximize the efficiency of the entire system for manufacturing an ester-based composition.

Particularly, the inventor of the present invention has found that when N number of reactors included in a reaction unit are connected in series, it is possible to optimize the entire system for manufacturing an ester-based composition by controlling the temperature of each reactor and an E value in each reactor to satisfy Formulas 1) and 2) above. Particularly, the inventor of the present invention has confirmed that when the above Formulas are satisfied, the amount of an ester-based composition to be manufactured may be maximized and the amount of the composition to be manufactured per unit time may also be maximized while the amount of wasted reaction raw materials is minimized.

The E value means, based on the "amount of a first alcohol required to allow a polycarboxylic acid initially injected to be reacted to 100%," the ratio of the amount of a first alcohol additionally injected to the amount of a first alcohol required to allow a polycarboxylic acid injected into each reactor to be reacted to 100%." The amount means an amount based on moles. For example, when a polycarboxylic acid is a dicarboxylic acid, and the dicarboxylic acid is injected in an amount of 100 moles and alcohol is injected in an amount of 300 moles into a reactor, the amount of alcohol for allowing the dicarboxylic acid to react to 100% is 200 moles, and thus, the amount of alcohol to be additionally injected is 100 moles. Therefore, an E value, which is a ratio thereof, corresponds to 50%, which is a ratio of 100 moles to 200 moles.

Meanwhile, the lower limit of $E_1$ may be −30%, −20%, −10%, 0%, or 10%, and the upper limit of $E_1$ may be 80%, 70%, 60%, 50%, or 40%. The lower limit of $E_n$ may be −10%, 0%, or 10%, and the upper limit of $E_n$ may be 80%, 70%, 60%, 50%, or 40%. When $E_1$ and $E_N$ are too low or too high, two reaction raw materials are not balanced, so that some reaction raw materials are wasted, and as a result, a composition may not be manufactured in a maximum amount. Particularly, when the E value of a first reactor is too high, alcohol is injected in excess amount from the beginning, resulting in a large amount of alcohol which does not participate in a reaction. In this case, a desired degree of conversion rate is not achieved, or too much energy is consumed to heat the alcohol not participating in the reaction, so that there may be a problem of deteriorating the efficiency of the entire reaction process. Furthermore, the volume of excess alcohol above a certain amount occupying inside the reactor may cause the reduction in yield of an ester-based composition product to be finally manufactured.

In the reaction unit, the lower limit of $T_1$ may be 100° C., 120° C., 140° C., 160° C., or 180° C., and the upper limit of $T_1$ may be 220° C. or 200° C. In addition, the lower limit of $T_n$ may be 140° C., 160° C., 180° C., 200° C., or 220° C., and the upper limit of $T_n$ may be 220° C., 230° C., 240° C., or 250° C. When $T_1$ and $T_N$ are too low, heat is not sufficiently supplied during a reaction, resulting in an insufficient conversion rate. When too high, the loss of reaction raw materials may be great due to the vaporization or the like of alcohol.

Meanwhile, the variable control unit serves to control the temperature and the E value in each reactor. Specifically, in terms of controlling the temperature, the variable control unit may be provided with a means for controlling the temperature by adjusting the amount of steam and the like which are consumed for heating each reactor. Also, in terms of controlling the E value, the variable control unit may be provided with a means for 1) controlling such that some of alcohol is removed or some amount of alcohol is injected between each reactor when a reaction mixture is continuously passed through reactors, 2) controlling the injection path and injection amount of a first alcohol stream formed from a mixed alcohol separation column to be described later, or 3) controlling such that some of alcohol refluxed from each reactor is removed or some amount of alcohol is added. In the case of 1), the variable control unit may be a decompression apparatus which is provided between a plurality of reactors connected in series to selectively remove alcohol, or a pump capable of additionally injecting alcohol between reactors. In the case of 2), the variable control unit may be a transfer pipe for connecting a mixed alcohol separation column and each reactor and may be provided with a pump or the like capable of controlling an injection amount into each reactor. In the case of the 3), the variable control unit may be a decompression apparatus or a pump which may be additionally connected to a reflux system connected to a reactor to remove some alcohols or additionally inject some alcohols in a reflux process. In addition to the above-listed apparatuses, any apparatus known to those skilled in the art may be used as the variable control unit of the present invention as long as the apparatus may perform the function of controlling the E value and temperature of each reactor.

When applying the above-described reaction unit, N may be an integer of 2 or greater, preferably an integer of 3 or greater, more preferably an integer of 3 to 10, 3 to 7, or 3 to 5. When the number of reactors is less than the above, a technical advantage of disposing a plurality of reactors in series may not be prominent, and when the number of reactors is too high, the number of reactors is too large, the process variable adjustment in each reactor becomes complex and costs consumed for relevant equipment including the reactors becomes large, so that it may be rather inefficient in terms of the costs for the entire process.

(2) When Provided With Plurality of Reactors Connected in Parallel

According to another embodiment of the present invention, the reaction unit includes N number of reactors in which a first reactor to an N-th reactor are connected in parallel and a supply control unit, wherein the supply control unit controls the injection amount and the injection path of the reaction mixture injected from the mixing unit into the reaction unit such that the formation of the first unpurified product mixture in each reactor is performed semi-continuously across the N number of reactors, and N may be an integer of 2 or greater.

When a plurality of batch reactors are used in a typical reaction process of the prior art, the batch reactors are disposed in parallel, such that reaction raw materials are simultaneously injected into the plurality of batch reactors, and then a reaction is simultaneously performed in each batch reactor after all of the reaction raw materials are injected. In this case, the injection of raw materials into each batch reactor is stopped during the performance of the reaction, and when the reaction is completed in each batch reactor, reaction products are simultaneously discharged from all of the batch reactors, during which the reaction is also not performed in each batch reactor. Therefore, it is not possible to implement a complete continuous manufacturing process with a batch reactor. In particular, in the case of a reaction process using a typical batch reactor, although a large amount of reaction products could be stably manufactured at one time, a reactor is not operated during a process in which reaction raw materials are injected or the reaction products are discharged, so that there is a disadvantage in terms of the efficiency of the entire process.

Therefore, the inventor of the present invention has confirmed that by allowing a plurality of batch reactors to be used sequentially, that is, semi-continuously, as in the above embodiment, reaction products may be continuously manufactured while maintaining the stability of a batch reactor.

Specifically, when the reaction unit 2 according to the embodiment is used, the reaction mixture 13 is sequentially injected into the N number of reactors, and each reactor into which the reaction mixture 13 is injected is heated to complete a reaction. After the reaction is completed, each reactor also sequentially discharges reaction products.

For example, the reaction unit 2 may be operated in the following manner:

1) A reaction mixture uniformly mixed in a mixing unit is injected into a first reactor, and after a predetermined amount of the reaction mixture is injected into the first reactor, the injection is stopped.

2) After the injection is stopped, the first reactor is heated to perform a reaction, and the mixing unit injects the reaction mixture into a second reactor.

3) After a predetermined amount of the reaction mixture is injected into the second reactor, the injection is stopped. After this point, the second reactor is heated to perform a reaction, and the mixing unit injects the reaction mixture into a third reactor.

4) N number of reactors sequentially manufacture reaction products in the above manner, and after the reaction mixture is injected into an N-th reactor, the reaction mixture is injected back into the first reactor. Also, reaction products manufactured after the reaction is completed are sequentially discharged in the same manner.

In addition, by setting reaction duration in one reactor and N, which is the total number of reactors, as input values and by setting a time interval from when a reaction mixture is injected into a first reactor to when the reaction mixture is injected into a second reactor as an output value, the supply control unit controls an injection path of the reaction mixture to be changed from a previous reactor to a next reactor at an interval of the output time interval, wherein the time interval may be 90% to 110% of a value obtained by dividing the reaction duration by N.

The supply control unit in the manufacturing system of the present invention should determine the injection path of the reaction mixture such that N number of reactors may operate sequentially. If the injection path of the reaction mixture is controlled at the time interval described above, at the time when reaction products are all or almost discharged after the reaction is completed in each reactor, the reaction mixture is started to be injected back into a corresponding reactor, so that all of the reactors may be operated without being stopped, and the efficiency of the process may be increased.

The above-described reaction duration is a sum of the amount of time consumed for the reaction and the amount of time consumed for the injection of the reaction mixture and the discharge of the reaction products. For example, when 30 minutes are consumed for the reaction, and 15 minutes are consumed for each of the injection of the reaction mixture and the discharge of the reaction products, the reaction duration is 60 minutes. In this case, if there are four reactors, the injection time interval for each reactor is 15 minutes, so that the reaction mixture is injected into each reactor every 15 minutes.

When applying the above-described reaction unit, the reaction unit injects a reaction mixture into each reactor, raises temperature, performs a reaction, and discharges reaction products all at the same time, so that at least one of a plurality of reactors should receive the reaction mixture continuously, at least another one of the plurality of reactors should perform the reaction, and at least another one of the plurality of reactors should discharge the reaction products. Accordingly, N may be an integer of 2 or greater, preferably an integer of 3 or greater, more preferably an integer of 3 to 10, 3 to 7, or 3 to 5. If there are too many reactors, a variety of additional equipment facilities are needed, including a supply control unit for controlling a reaction mixture to be injected into each reactor in order and reaction products to be discharged from each reactor. Furthermore, reaction duration per one reactor may be shorter than the sum of the injection time of the raw materials injected into a reactor and the discharge time of reaction products, so that there may be time during which the reactor does not operate before receiving raw materials, which may result in adverse effects on productivity. In addition, the space required for the placement of each reactor becomes also excessive, which may be inefficient in terms of costs of the entire process.

Meanwhile, when the reaction unit includes a plurality of reactors connected in series and a plurality of reactors connected in parallel, each reactor may be provided with a reflux system. Since the temperature at which an esterification reaction is performed is a temperature at which a first alcohol and water, which is a by-product of the esterification reaction, may be vaporized, the first alcohol and the water may vaporize continuously during the reaction. The vaporization of the first alcohol, which is a reaction raw material, lowers the concentration of the first alcohol in a reaction mixture, which caused the decrease in reaction rate. Therefore, it is necessary to re-liquefy the first alcohol to be vaporized and then inject the re-liquefied first alcohol into a reactor, and each reactor may be provided with a reflux system for the above.

Specifically, the reflux system may be provided with a gas-liquid separation column connected to an upper portion of a reactor and separating alcohol and water discharged through the upper portion of the reactor, a condenser for cooling a gas discharged through an upper line of the gas-liquid separation column, and a decanter for separating a liquid discharged through a lower line of the gas-liquid separation column and a liquid condensed in the condenser into different layers recirculating the alcohol into the reactor.

As described above, when a reactor is provided with the reflux system, it is possible to increase the efficiency and economic feasibility of the reaction by re-liquefying alcohol vaporized during the reaction and re-injecting the re-liquefied alcohol into the reactor, and at the same time, it is possible to allow the reaction to proceed towards a forward reaction by removing water, which is a by-product of an esterification reaction, that is, allowing a high conversion rate to be achieved.

Trans-Reaction Unit

The above-described first unpurified product mixture formed in the reaction unit is then subjected to a trans-esterification reaction with a second alcohol 31 in a trans-reaction unit 3.

Specifically, a trans-esterification reaction is performed between the first ester compound included in the first unpurified product mixture and the second alcohol, and as a result, a second unpurified product mixture 32 including a second ester compound is formed.

The second alcohol may be injected directly into the trans-reaction unit, or may be injected directly into the first unpurified product mixture before the first unpurified product mixture is injected into the trans-reaction unit and then mixed.

An ester-based compound to be finally obtained through the trans-esterification reaction in the trans-reaction unit may include two or more kinds of ester compounds.

The type or shape of the trans-reaction unit is not particularly limited as long as trans-reaction unit is for performing the trans-esterification reaction between the first unpurified product mixture and the second alcohol, and the reaction unit described above may also be applied as the trans-reaction unit of the present invention. For example, the trans-reaction unit may be a single reactor, or a plurality of reactor connected in series or in parallel, and may include heating means for controlling the temperature in the reactor, and the like.

Neutralization Unit

The second unpurified product mixture produced in the trans-reaction unit is then transferred to a neutralization unit 4 to be subjected to neutralization and water separation, and as a result, a water layer stream 42 and an organic layer stream 41 are formed.

In a typical process for purifying a product of an esterification reaction, when the reaction is completed, neutralization is performed to preferentially deactivate a catalyst and after the neutralization, the extraction of alcohol is performed under reduced pressure in a reactor or a distillation device in which the esterification reaction has been performed. This is a method which has been commonly performed since there is an advantage of being highly efficient in separating an unreacted alcohol from an ester product. In addition, since the extraction is performed under reduced pressure after the neutralization due to the structure of a facility, it is common that water is removed together with an alcohol mixture from an upper portion of the facility.

As described above, when the water is mixed with the alcohol mixture, specifically alcohol having a small number of carbon atoms, and then separated, the alcohol having a small number of carbon atoms is highly soluble in water, so that it is difficult to separate the alcohol. Also, the alcohol having a small number of carbon atoms accounts for more than about 3.0 wt % of the entire stream, and thus, may cause a problem of being classified as a serious level of wastewater if not suitably treated, thereby incurring a significant amount of costs and energy. In addition, in an effort to reduce the content of alcohol in the wastewater, a de-alcoholization process may performed to extract unreacted alcohol under reduced pressure immediately after the reaction is completed.

Accordingly, in the manufacturing method according to the present invention, a neutralizer having a partition wall structure is introduced into the neutralization unit, and through the introduction of the neutralizer, a water separation process (layer separation) may be performed to a significant degree along with a neutralization process. When neutralization and water separation are performed through the neutralizer according to the present invention, the alcohol mixture may be sent to an organic layer rich in ester, and thus, the amount of alcohol, especially lower alcohol, leaked to a water layer may be minimized. Specifically, the neutralization unit includes or more neutralizers, and the inner space of the neutralizer is provided with one or more partition walls such that the inner space is divided into a neutralization space and a layer separation space in the left and right directions respectively and a passage connecting the two spaces is formed, and the passage may start from an upper portion of the neutralization space.

Typically, water and alcohol should be separated in a state in which ester is not present. However, according to the present invention, layer separation is performed in a state in which ester is present, thereby inducing alcohol into the organic layer, so that there is an advantage of minimizing the amount of alcohol contained in water. In a water layer which has been subjected to layer separation, alcohol may be included in an amount of 0.5-3.0 parts by weight based on 100 parts by weight of the mixed weight of water and alcohol. Substantially, the alcohol may be 2.0 parts by weight or less, even more substantially 1.0 parts by weight or less, and the content of alcohol in the wastewater may be reduced compared to a typical process.

Meanwhile, in the purifying step according to the present invention, the second unpurified product mixture may include 50-95 parts by weight of ester and 5-50 parts by weight of alcohol, and since a step of removing unreacted alcohol is not performed, the content of an alcohol component may be somewhat greater than that of ester, which is a product.

According to an embodiment of the present invention, since the neutralizer has a partition wall structure, an entire process may be operated continuously. The structural properties of the partition wall structure are not particularly limited. However, one or more partition walls should be installed such that the space inside the neutralizer is separated into at least two spaces and a passage for connecting the two spaces is provided.

Specifically, the neutralizer includes a first space provided on an injection port side and a second space provided on a discharge portion side of the organic layer stream, wherein a passage between the two spaces is provided in the vertical direction such that an upper portion of the neutralization space and a lower portion of the layer separation space are connected, and the one or more partition walls may form the passage. Also, the neutralizer may further include a neutralization agent injection port through which the neutralization agent is introduced into the first space and a waste liquid treatment port from which a waste liquid is discharged from the second space.

In addition, an entrance stream (injection port) of the neutralizer through which the organic layer stream and the unpurified product mixture of the neutralizer are flowing may be where mutual heat exchange is achieved. The neutralization reaction is a heat generating reaction. However, the unpurified product mixture which has been subjected to the esterification reaction needs cooling since the unpurified product mixture is introduced while being at a high temperature due to a high reaction temperature and the organic layer stream to be injected into a distillation unit to be described later needs heating for distillation, energy consumption may be reduced by utilizing unnecessary heat of the entrance stream of the neutralizer as heat required for the exit stream thereof.

According to an embodiment of the present invention, the second unpurified product mixture is neutralized in the neutralizer, and a neutralization agent may be injected thereinto to perform the neutralization. The neutralization agent may be a basic aqueous solution having a base concentration of 0.1-50 wt %, and may be, for example, a sodium hydroxide aqueous solution or a sodium hydrogen carbonate aqueous solution. A basic aqueous solution having the base concentration as described above may be applied as the neutralization agent, and the neutralization of a catalyst and the neutralization of reaction products may be performed using the same. Accordingly, a salt generated from the neutralization may be discharged through the waste liquid treatment port.

The second unpurified product mixture may be injected into a neutralizer and added with a basic aqueous solution, which is a neutralization agent, to neutralize both a catalyst and reaction products, and may be separated into an organic layer stream and a water layer stream, wherein the organic layer stream may be rich in ester but contain alcohol and the water layer stream may be rich in alcohol and contain a trace of ester.

Here, the organic layer stream may include 50-95 parts by weight of ester and 5-50 parts by weight of alcohol, and most of the alcohol may be separated during neutralization and water separation processes. The alcohol may include both the first alcohol and the second alcohol, but most of the alcohol is higher alcohol. Since lower alcohol is more hydrophilic than ester or the higher alcohol, most of the lower alcohol may be separated into the water layer.

In addition, first and second spaces separated due to a partition wall of the neutralization unit and a passage are formed, so that the second unpurified product mixture introduced is neutralized with a basic aqueous solution to form a salt in the first space, and a predetermined amount is moved through the passage to the second space to induce layer separation. As the layer separation is achieved in the second space, the organic layer is continuously raised to discharge the organic layer stream from an upper end of the second space, and the water layer stream containing the salt and the lower alcohol is discharged through the waste liquid treatment port provided on a lower portion of the second space.

The neutralization and water separation performed in the neutralizer may be performed in a range of about 30-150° C., and the capacity of the neutralizer may be about 5-300 m$^3$. As other features not described in this specification, those applied in the art may be applied without being specifically limited.

Distillation Unit

An organic layer stream 41 of a water layer stream 42 and the organic layer stream 41 formed by neutralizing and water-separating the second unpurified product mixture in the neutralization unit 4 above is then transferred to a distillation unit 5, and the first alcohol and the second alcohol remaining in the distillation unit are removed in the form of an alcohol-rich stream 52 to form an ester-rich stream 51.

A column may be applied to the distillation unit. However, reduced pressure extraction may be applied in equipment in the form of a drum, and any equipment capable of removing alcohol may be applied without particular limitation. Also, when a column is installed, a buffer tank may be installed at the front end thereof as additional equipment. However, a piece of equipment such as a flash drum in the form of a drum may be preferably installed to function to control the loading amount of a product purifying unit at the rear end thereafter.

That is, in the organic layer stream formed in the neutralization unit may include ester such as a first ester compound and/or a second ester compound, a first alcohol, and a second alcohol, and when alcohol is removed in a distiller, only lower alcohol having the lowest boiling point may be easily separated with only a small amount of energy, and at the same time, there may be an advantage in that the loading amount of the product purifying unit at the rear end may be controlled.

At this time, the alcohol-rich stream separated from the upper portion of the distillation unit may include 50-100 parts by weight of lower alcohol and 0-50 parts by weight of higher alcohol based on 100 parts by weight of all materials in the alcohol-rich stream, and the ester-rich stream separated from the lower portion thereof may include 50-99 parts by weight of ester and 1-50 parts by weight of higher alcohol based on 100 parts by weight of all materials in the ester-rich stream.

The distillation unit may have a capacity of about 10-300 $m^3$, may perform separation at about 30-200° C., and may be applied to pressure conditions of from normal pressure to a reduced pressure level of 10 mmHg. This range is a level which allows a purifying process to be performed normally and efficiently, and if the above range is satisfied, distillation may be efficiently performed.

Product Purifying Unit

Of the alcohol-rich stream 52 and the ester-rich stream 51 formed in the distillation unit above, the ester-rich stream is then transferred to a product purifying unit 6, and traces of the first alcohol and the second alcohol remaining in the ester-rich stream are removed in the form of a mixed alcohol stream 62, and the rest of the stream including ester is obtained as the final product, which is a product stream 61.

The product purifying unit of the present invention may remove a trace of alcohol remaining in the ester-rich stream through an upper portion and separate an ester-based composition to be commercialized from a lower portion. Distillation using steam may also be performed in the product purifying unit, and the product purifying unit may be in the form of a column or a drum, but may be preferably a column.

The product purifying unit may have a capacity of about 10-300 $m^3$, may perform at 30-200° C., and may be applied to pressure conditions of from normal pressure to a reduced pressure level of 10 mmHg. This range is a level which allows a purifying process to be performed normally and efficiently, and if the above range is satisfied, purifying may be efficiently performed.

A product stream separated from the lower portion of the product purifying unit is commercialized, and the mixed alcohol stream separated to the upper portion may be transferred to a mixed alcohol tank or a mixed alcohol separation column to be described later and used.

In addition to the mixing unit, the reaction unit, the trans-reaction unit, the neutralization unit, the distillation unit, and the product purifying unit, the system for manufacturing an ester-based composition provided by the present invention may further include a mixed alcohol tank 7, a mixed alcohol separation column 8, and/or a wastewater treatment unit 9.

Mixed Alcohol Tank

As described above, the distillation unit may form an alcohol-rich stream and the product purifying unit may form a mixed alcohol stream, and the alcohol-rich stream and the mixed alcohol stream may include relatively a large amount of a first alcohol and a second alcohol. Accordingly, when the mixed alcohol stream and the alcohol-rich stream are separated and used as reaction raw materials, the overall economic feasibility and efficiency of the process may be increased.

Figure 2:
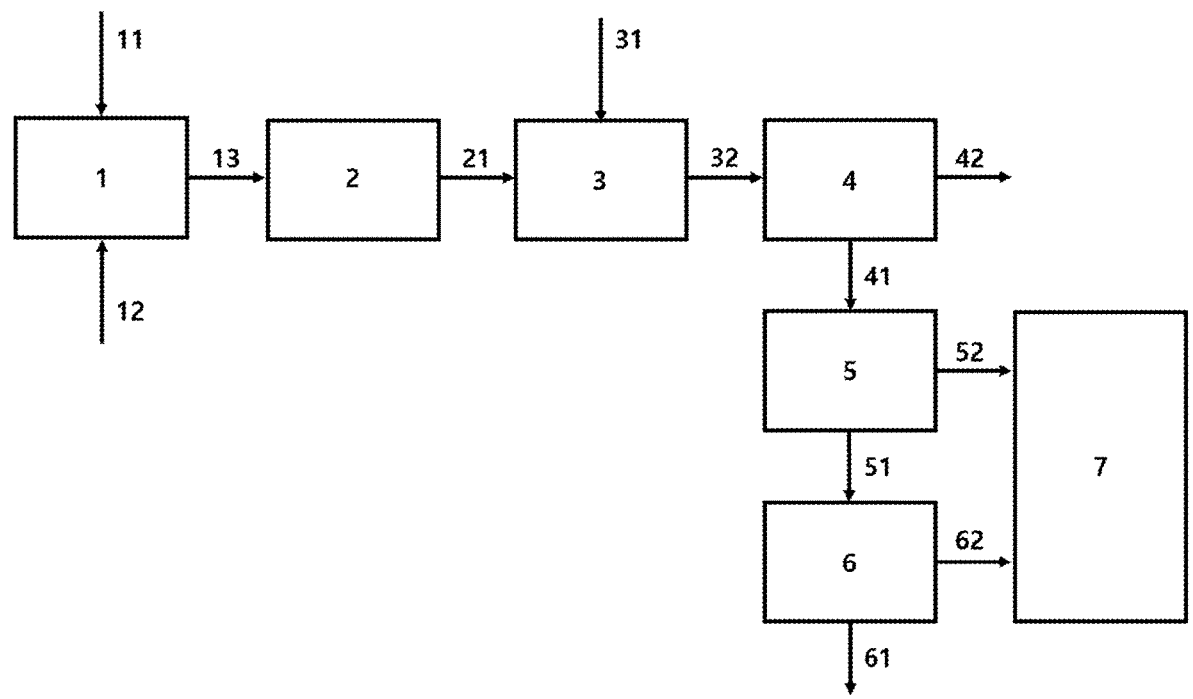
FIG. 2 is a schematic diagram illustrating a system for manufacturing an ester-based composition of the present invention, the system including a mixing unit, a reaction unit, a trans-reaction unit, a neutralization unit, a distillation unit, a product purifying unit, and a mixed alcohol tank.

Therefore, as described in FIG. 2, the system for manufacturing an ester-based composition of the present invention may further include a mixed alcohol tank for receiving and storing the mixed alcohol stream and the alcohol-rich stream. The mixed alcohol tank may serve to store the mixed alcohol stream and the alcohol-rich stream without separating the first alcohol and the second alcohol contained therein, and if necessary, the mixed alcohol stream and the alcohol-rich stream may be suitably treated and used later.

For example, a mixture of the mixed alcohol stream and the alcohol-rich stream stored in the mixed alcohol tank may be transferred to a mixed alcohol separation column in the form of a first recovery alcohol stream, which is to be described later.

The size or shape of the mixed alcohol tank is not particularly limited as long as the mixed alcohol tank may perform the function of storage, and a mixed alcohol tank in a drum or tank shape widely used in a reaction process field may be applied.

Mixed Alcohol Separation Column

Figure 3:
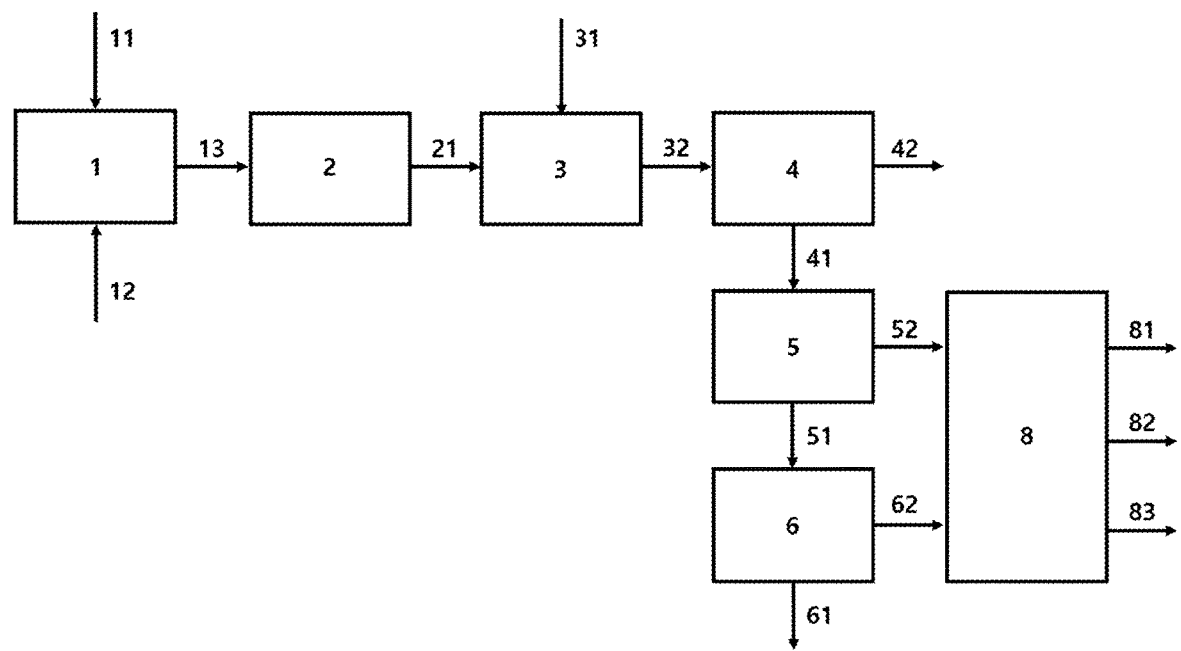
FIG. 3 is a schematic diagram illustrating a system for manufacturing an ester-based composition of the present invention, the system including a mixing unit, a reaction unit, a trans-reaction unit, a neutralization unit, a distillation unit, a product purifying unit, and a mixed alcohol separation column.

As described with reference to the mixed alcohol tank, the first alcohol and the second alcohol remaining in the alcohol-rich stream and the mixed alcohol stream need to be utilized, and by injecting the same into a mixed alcohol separation column, the first alcohol and the second alcohol may be separated. Therefore, as described in FIG. 3, the manufacturing system of the present invention may further include a mixed alcohol separation column 8.

Specifically, the mixed alcohol separation column 8 may receive the alcohol-rich stream formed in the distillation unit and the mixed alcohol stream formed in the product purifying unit to form a first recovery alcohol stream (not shown), and may separate the first recovery alcohol stream into a water stream 83, a first alcohol stream 81, and a second alcohol stream 82. The first recovery alcohol stream refers to a stream in the mixed alcohol separation column, and is not separately shown in the figures.

The mixed alcohol separation column should be able to separate water, a first alcohol, and a second alcohol from each other, and may be, for example, in the form of a distillation column. In addition, the distillation column may be designed to have multiple stages to accurately separate each material. In addition, any device may be applied as the mixed alcohol separation column of the present invention without particular limitation as long as the device may separate a mixture in a liquid state using a boiling point difference.

The first alcohol and the second alcohol separated from the mixed alcohol separation column may be injected into reaction unit or the trans-reaction unit as reaction raw materials and used, and may be separately obtained and used in a separate manufacturing system other than the manufacturing system of the present invention. When the first alcohol stream and the second alcohol stream separated are used again in the manufacturing system of the present invention, the first alcohol stream and the second alcohol stream may be directly injected into the reaction unit and the trans-reaction unit, or may be injected into the mixing unit or the first unpurified product mixture in a previous state. In addition, the higher alcohol between the first alcohol and the second alcohol may be injected to a wastewater treatment unit as described later and used as an additive. Meanwhile, the water stream may be discharged as wastewater or may be injected into the wastewater treatment unit to be described later to be subjected to wastewater treatment.

Meanwhile, the alcohol-rich stream and the mixed alcohol stream may be directly injected into the mixed alcohol separation column from the distillation unit and the product purifying unit, respectively, or may be pre-mixed though the mixed alcohol tank described above and then injected thereinto. When injected through the mixed alcohol tank, the alcohol-rich stream and the mixed alcohol stream are pre-mixed and then injected, so that the separation thereof in the mixed alcohol separation column may be smoothly performed, and there is also an advantage in that the temperature control before the injection into the mixed alcohol separation column is easy.

Wastewater Treatment Unit

Figure 4:
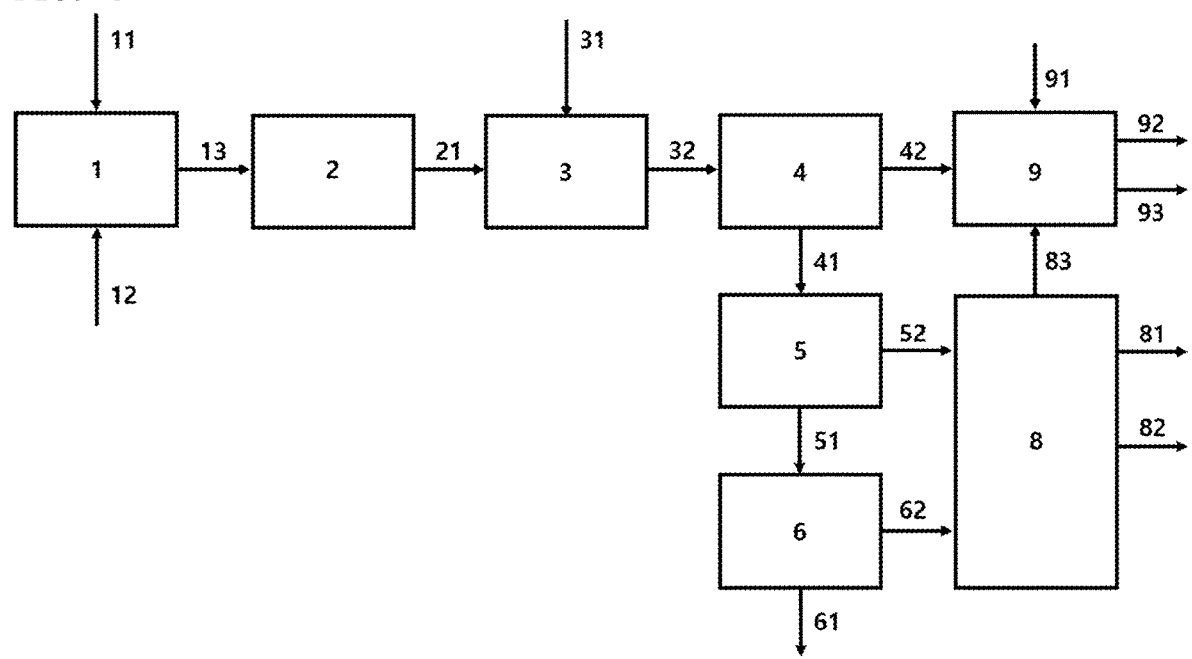
FIG. 4 is a schematic diagram illustrating a system for manufacturing an ester-based composition of the present invention, the system including a mixing unit, a reaction unit, a trans-reaction unit, a neutralization unit, a distillation unit, a product purifying unit, a mixed alcohol separation column, and a wastewater treatment unit.

As described in FIG. 4, the system for manufacturing and ester-based composition of the present invention may further include a wastewater treatment unit 9 in addition to the mixed alcohol separation column described above. The wastewater treatment unit may receive the water layer stream of the neutralization unit and the water stream 83 separated in the mixed alcohol separation column to form a preliminary wastewater stream, and may add a high alcohol 91 having a larger number of carbon atoms between the first alcohol sand the second alcohol to the preliminary wastewater stream to form a second recovery alcohol stream 92 including the first alcohol and the second alcohol, and a wastewater stream 93.

The higher alcohol additionally injected into the wastewater treatment unit serves as an additive for separating lower alcohol dissolved in water to a high solubility, and as the lower alcohol is dissolved in the higher alcohol additionally injected instead of water, the content of the lower alcohol in water is reduced. The lower alcohol dissolved in the higher alcohol instead of water, that is, the second recovery alcohol stream, is present in a state in which the higher alcohol and the lower alcohol are mixed, and since the higher alcohol and the lower alcohol correspond to the first alcohol and the second alcohol used as reaction raw materials in the manufacturing system of the present invention, the higher alcohol and the lower alcohol may be used again in the present invention after being subjected to subsequent treatment. Meanwhile, as described above, the higher alcohol between the first alcohol and the second alcohol separated from the mixed alcohol separation column may be used as the higher alcohol to be injected to the wastewater treatment unit.

The wastewater treatment unit performs layer separation using low solubility between water and higher alcohol, and layer separator equipment used in a reaction process field may be applied thereto. Any equipment may be used as the wastewater treatment unit of the present invention without particular limitation as long as the equipment uses the above separation principle in which an organic phase and a water phase are not smoothly mixed. More specifically, a piece of equipment having a structure substantially the same as that of the neutralization unit described above may be applied as the wastewater treatment unit.

The second recovery alcohol stream formed in the wastewater treatment unit of the present invention may be transferred back to the mixed alcohol tank or the mixed alcohol separation column to be used. In addition, the wastewater stream formed through the present wastewater treatment unit may include the lower alcohol in an amount of 3.0 wt % or less, 0.01-3.0 wt %, 0.01-2.0 wt %, or 0.01-1.0 wt% based on the total weight of the wastewater stream, or may substantially include no lower alcohol.

Catalyst Injection Unit

The system for manufacturing an ester-based composition of the present invention may further include a catalyst injection unit. The esterification reaction and the trans-reaction reaction performed in the manufacturing system of the present invention may be further facilitated in the presence of a catalyst. Therefore, a catalyst injection unit may be further included to inject a catalyst directly into the reaction unit and the trans-reaction unit, or into the reaction mixture before being injected into the reaction unit or the trans-reaction unit or the first unpurified product mixture.

The specific shape and position of the catalyst injection unit may vary depending on the type or state of a catalyst to be used. However, those skilled in the art may appropriately select the shape or the position of the catalyst injection unit in terms of implementing a function of injecting a catalyst into the reaction mixture or the first unpurified product mixture.

Filtering Unit

The system for manufacturing an ester-based composition of the present invention may further include a filtering unit for removing solid impurities remaining in at least one of the reaction mixture, the first unpurified product mixture, the second unpurified product mixture, the organic layer stream, the ester-rich stream, and the product stream.

When a solid catalyst is used or impurities in the solid form of a reaction raw material are present, or when impurities in a solid form are generated during a reaction process, there is a need to remove the impurities in order to increase the quality of the final product. Accordingly, the present invention may further include a filtering unit for removing solid impurities in a stream.

A stream to be filtered by the filtering unit is not specifically limited, and the filtering unit may be applied to all streams moving between each component in the manufacturing system of the present invention. More specifically, in the system for manufacturing an ester-based composition of the present invention, the filtering unit may be applied to one or more steams selected from the reaction mixture, the first unpurified product mixture, the second unpurified product mixture, the organic layer stream, the ester-rich stream, and the product stream.

The position of the filtering unit varies depending on a stream to be filtered, and the shape or type of the filtering unit is not particularly limited as long as the filtering unit may remove solid impurities without the loss of an ester compound in the stream. For example, a filtering unit in a filter type may be applied.

Method for Manufacturing Ester-Based Composition

The present invention provides a method for manufacturing an ester-based composition which may be implemented by the above-described system for manufacturing an ester-based composition of the present invention.

Specifically, the method for manufacturing an ester-based composition, the method provided by the present invention, may include a step S1 of forming a reaction mixture of a polycarboxylic acid and a first alcohol, a step S2 of performing an esterification reaction of the reaction mixture to form a first unpurified product mixture including a first ester compound, a step S3 of performing a trans-esterification reaction of the first unpurified product mixture and a second alcohol to form a second unpurified product mixture including a second ester compound, a step S4 of performing the neutralization and water separation of the second unpurified product mixture to form a water layer stream and an organic layer stream, a step S5 of distilling the organic layer stream to obtain an alcohol-rich stream and an ester-rich stream, and a step S6 of removing the first alcohol and the second alcohol remaining in the ester-rich stream to obtain a mixed alcohol stream and a product stream.

Mixing Step (S1)

The step S1 is performed in the mixing unit of the manufacturing system of the present invention and is a step in which the mixing of a polycarboxylic acid and a first alcohol, which are reaction raw materials, is performed. A detailed method of the mixing is not particularly limited. However, when considering the fact the polycarboxylic acid and the first alcohol react in a liquid state, the mixing may be performed through a stirrer, a mixer, or the like. The rate, intensity, and duration of stirring during the mixing may vary depending on the flow rate or properties of reaction raw materials, and those skilled in the art may select an appropriate rate, intensity, and duration of stirring to perform the mixing.

Esterification Reaction Step (S2) and Trans Esterification Reaction Step (S3)

The step S2 is a step in which an esterification reaction between the first alcohol and the polycarboxylic acid included in the reaction mixture is performed, and Step S3 is a step in which a trans-esterification reaction between a first ester compound in a first unpurified product mixture and a second alcohol is performed.

Specific reaction conditions in the step S2 and S3 are not particularly limited, and the esterification reaction and the trans-esterification reaction may be performed under temperature and pressure conditions known under which an esterification reaction and a trans-esterification reaction are performed. In addition, at least one of the step S2 and S3 may be performed under the presence of a catalyst.

When a catalyst is used, there is an advantage in that a reaction may be completed faster, and the catalyst may be directly into the reaction mixture and/or the first unpurified product mixture, or may be injected into the reaction unit and/or the trans-reaction unit in which each reaction is performed. It is somewhat more preferable in terms of the efficiency of the entire process that the catalyst is directly added into the reaction mixture and/or the first unpurified product mixture.

The catalyst may be one or more selected from an acid catalyst such as sulfuric acid, hydrochloric acid, phosphoric acid, nitric acid, paratoluenesulfonic acid, methanesulfonic acid, ethanesulfonic acid, propanesulfonic acid, butanesulfonic acid, and alkyl sulfuric acid, a metal salt such as aluminum lactate, lithium fluoride, potassium chloride, cesium chloride, calcium chloride, iron chloride, and phosphoric acid, a metal oxide such as heteropoly acid, a natural/synthetic zeolite, a cation and anion exchange resin, and an organic metal such as tetraalkyl titanate and a polymer thereof, and may preferably be tetraalkyl titanate. As the tetraalkyl titanate, TiPT, TnBT, TEHT, or the like may be used, and it is preferable to use tetraalkyl titanate having an alkyl group same as the alkyl group of alcohol to be reacted as a ligand. For example, it is preferable to use tetrapropyl titanate for a reaction between propanol and terephthalic acid. When a catalyst having an alkyl group same as that of alcohol as a ligand is used, catalyst by-products which may be generated in a subsequent process are not generated or may be easily controlled even if generated.

The amount of a catalyst to be used may vary depending on the kind of the catalyst. In one example, a homogeneous catalyst may be used in an amount range of 0.001-5 wt %, 0.001-4 wt %, 0.01-3 wt %, or 0.01-2 wt % based on the total weight of the reaction mixture or the first unpurified product mixture, and a heterogeneous catalyst may be used in an amount range of 5-200 wt %, 5-150 wt %, 10-150 wt %, or 20-150 wt % based on the total weight of the reaction mixture or the first unpurified product mixture.

The step S2 may be performed differently depending on the type of the reactor described above. In one example, the step S2 may be performed in N number of reactors connected in series, wherein each reactor satisfies the following Formulas 1) and 2), and N may be an integer of 2 or greater:

$$T_{n1-1} \leq T_{n1} \quad (1)$$

$$E_{n2-1} \geq E_{n2} \geq E_1 \quad (2)$$

in Formulas above, n1 is an integer of 2 to N, and n2 is an integer of 3 to N.

$T_x$=Temperature of an x-th reactor $E_x$={(Number of moles of alcohol injected into an x-th reactor−c*Number of moles of dicarboxylic acid injected into an x-th reactor/c*Number of moles of dicarboxylic acid injected into the first reactor)*100%}, In $T_x$ and $E_x$, x is an integer of 1 to N, and c is the number of carboxylic acid groups contained in one molecule of the polycarboxylic acid.

In another example, the step S2 is performed in N number of reactors connected in parallel, and the formation of the first unpurified product mixture in each reactor may be performed semi-continuously across the N number of reactors, and N may be an integer of 2 or greater.

Since the case in which the step S2 is performed by the above-described two methods has been described in detail with reference to the manufacturing system above, a detailed description thereof will be omitted.

Neutralization Step (S4)

The step S4 is a step of neutralizing an acid catalyst remaining in a second unpurified product mixture and performing water separation to form an organic layer stream including an ester compound which is the final product and a water layer stream including impurities.

When a catalyst remains in an ester-based composition which is the final product, a problem of deteriorating quality occurs. Therefore, it is necessary to neutralize and remove the catalyst in the second unpurified product mixture.

As the neutralization agent, a basic aqueous solution having a base concentration of 0.1-50 wt % may be used. For example, a sodium hydroxide aqueous solution or a sodium hydrogen carbonate aqueous solution may be used.

Since the detailed implementation of the step S4 has been described in detail with reference to the manufacturing system above, a detailed description thereof will be omitted.

Distillation Step (S5) and Product Purifying Step (S6)

The step S5 and the step S6 are steps performed to remove alcohol remaining in the organic layer stream which has been subjected to neutralization and water separation. In the previous neutralization step, a water layer and an organic layer are separated, but since alcohol has affinity with both water and ester, a portion of the alcohol is esterified and present in the organic layer. Therefore, in order to further improve the quality of the final product, it is necessary to remove the alcohol in the organic layer. Firstly, an ester-rich stream is obtained through distillation, and secondly, the first alcohol and the second alcohol are removed in the ester-rich stream.

Since the detailed implementations of the steps S5 and S6 have been described in detail with reference to the manufacturing system above, detailed descriptions thereof will be omitted.

The method for manufacturing an ester-based composition of the present invention may further include an alcohol recovery step S7 and a wastewater treatment step S8.

Alcohol Recovery Step (S7)

In the method for manufacturing an ester-based composition of the present invention, the step S7 which may be further included is a step of mixing the alcohol-rich stream obtained in the step S5 and the mixed alcohol stream obtained in the step S6 to form a first recovery alcohol stream and separating the first recovery alcohol stream into a water stream, a first alcohol stream, and a second alcohol stream to form the water stream, the first alcohol stream, and the second alcohol stream.

Since the first alcohol and the second alcohol which are removed in the previous distillation and purifying steps correspond to reaction raw materials, when the first alcohol and the second alcohol are suitably treated and then used again as reaction raw materials, it is possible to improve the economic feasibility and efficiency of the entire process. To this end, in the step S7, the alcohol-rich stream obtained in the step S5 and the mixed alcohol stream obtained in the step S6 are recovered and mixed to form a first recovery alcohol stream, and the first recovery alcohol stream is separated into water, a first alcohol and a second alcohol to be used again. The separation in the present step may be performed in the mixed alcohol separation column of the above-described manufacturing system.

Specifically, a first alcohol stream obtained in the present step may be used as the first alcohol in the step S1, and a second alcohol stream obtained in the present step may be used as the second alcohol in the step S2. In addition, alcohol having a larger number of carbon atoms between the first alcohol and the second alcohol, that is higher alcohol, may be transferred to the wastewater treatment unit to be used as an additive in a wastewater treatment step to be described later. Since the detailed description about the implementation of the present step other than the above has been described in detail with reference to the manufacturing system above, a detailed description thereof will be omitted.

Wastewater Treatment Step (S8)

In the method for manufacturing an ester-based composition of the present invention, a step which may be further included together with the step S7 may be a step S8 of mixing the water layer stream obtained in Step S4 and the water stream obtained in the step S7 to form a preliminary wastewater stream and adding alcohol having a larger number of carbon atoms between the first alcohol and the second alcohol to the preliminary wastewater stream to form a second recovery alcohol stream including the first alcohol and the second alcohol, and a wastewater stream.

In the previous neutralization step and the alcohol recovery step, a large amount of water is obtained. However, the lower alcohol having a smaller number of carbon atoms between the first alcohol and the second alcohol is highly soluble in water, and thus, and may be dissolved and present in the large amount of water. In general, the large amount of water should be discharged immediately and treated as wastewater. However, the high alcohol content in wastewater may cause environmental problems, so that it is necessary to reduce the alcohol content in the wastewater by treating the same in advance. To this end, the present step S8 may be applied.

In the present step, the water layer stream obtained in the step S4 and the water stream obtained in the step S7 are mixed to form a preliminary wastewater stream and higher alcohol having a larger number of carbon atoms between the first alcohol and the second alcohol are injected to the preliminary wastewater stream as an additive. Lower alcohol having a small number of carbon atoms is highly soluble in water, but is also highly soluble in higher alcohol having a large number of carbon atoms, and thus, may be separated from the water and dissolved as the additive. The additive is not mixed well with water, and thus, may form an additional layer from water. Therefore, a mixed alcohol layer and a wastewater layer may be separated by simple layer separation.

The reason for using the high alcohol between the first alcohol and the second alcohol corresponding to reaction raw materials as the additive instead of using other organic solvents is that most of organic layer components obtained when the first alcohol or the second alcohol is used as the additive are composed of the first alcohol and the second alcohol and the mixed alcohol may be separated together with a mixed alcohol obtained in another step since they both have the same compositions. When a separate organic solvent is used as an additive, there may be a problem in that an additional means for treating alcohol mixed in the organic solvent are required.

Although the amount of an additive added in the present step is not particularly limited, the additive may be used in a small amount with respect to the amount of the preliminary wastewater stream since the concentration of alcohol in the preliminary wastewater stream is not very high. The specific amount of an additive may vary depending on the types of the first alcohol and the second alcohol or the flow rate of the preliminary wastewater stream. Those skilled in the art may select an appropriate amount of additive to perform the present step. Since the detailed description about the implementation of the present step other than the above has been described in detail with reference to the manufacturing system above, a detailed description thereof will be omitted.

In addition to the above-described steps, according to an embodiment of the present invention, the manufacturing method of the present invention may further include a step of removing solid impurities by passing a stream through a filter.

The filtering step may be performed on a stream between each step. Any method known in the art may be applied to the filtering without particular limitation, and the filtering may be performed using filters of various materials, and the like.

In the method for manufacturing an ester-based composition of the present invention, the number of carbon atoms of the first alcohol may be greater than the number of carbon atoms of the second alcohol. When the manufacturing method of the present invention is used, since a trans-esterification reaction is performed after an esterification reaction, it is preferable to subject alcohol having a large number of carbon atoms to the esterification reaction, and then subject alcohol having a small number of carbon atoms to the trans-esterification reaction. When the reaction is performed in the above order, the trans-esterification reaction at a later stage is easily performed, and the content of each ester in an ester-based composition, which is the final product, may be smoothly controlled.

In the method for manufacturing an ester-based composition of the present invention, the steps S1 to S6 may be continuously performed, and even when the step S7 and/or the step S8 are included in addition thereto, the entire manufacturing method may be continuously performed. As described above with reference to the manufacturing system, all components constituting the manufacturing system of the present invention may be continuously operated, and accordingly, all the steps may also be performed continuously.

DESCRIPTION OF THE REFERENCE NUMERALS OR SYMBOLS

1: Mixing unit
11: First alcohol
12: Polycarboxylic acid
13: Reaction mixture

2: Reaction unit
21: First unpurified product mixture
3: Trans-reaction unit
31: Second alcohol
32: Second unpurified product mixture
4: Neutralization unit
41: Organic layer stream
42: Water layer stream
5: Distillation unit
51: Ester-rich stream
52: Alcohol-rich stream
6: Product purifying unit
61: Product stream
62: Mixed alcohol stream
7: Mixed alcohol tank
8: Mixed alcohol separation column
81: First alcohol stream
82: Second alcohol stream
83: Water stream
9: Wastewater treatment unit
91: Higher alcohol between first alcohol and second alcohol
92: Second recovery alcohol stream
93: Wastewater stream

The invention claimed is:

1. A system for manufacturing an ester-based composition, the system comprising:
a mixing unit in which a reaction mixture of a polycarboxylic acid and a first alcohol is formed;
a reaction unit in which an esterification reaction of the reaction mixture is performed to form a first unpurified product mixture including a first ester compound;
a trans-reaction unit in which a trans-esterification reaction of the first unpurified product mixture formed in the reaction unit and a second alcohol separately injected is performed to form a second unpurified product mixture including a second ester compound;
a neutralization unit in which the neutralization and water separation of the second unpurified product mixture are performed to form a water layer stream and an organic layer stream;
a distillation unit in which an alcohol-rich stream and an ester-rich stream are formed by distilling the organic layer stream;
a product purifying unit for removing the first alcohol and the second alcohol remaining in the ester-rich stream to form a mixed alcohol stream including the first alcohol and the second alcohol and a product stream;
a mixed alcohol separation column for receiving the alcohol-rich stream formed in the distillation unit and the mixed alcohol stream formed in the product purifying unit to form a first recovery alcohol stream, and separating the first recovery alcohol stream into a water stream, a first alcohol stream, and a second alcohol stream; and
a wastewater treatment unit for receiving the water layer stream of the neutralization unit and the water stream separated from the mixed alcohol separation column to form a preliminary wastewater stream, and adding alcohol having a larger number of carbon atoms between the first alcohol and the second alcohol to the preliminary wastewater stream to form a second recovery alcohol stream including the first alcohol and the second alcohol, and a wastewater stream.

2. The system of claim 1, wherein the second recovery alcohol stream is transferred to the mixed alcohol separation column and recovered.

3. The system of claim 1, wherein the reaction unit comprises N number of reactors in which a first reactor to an N-th reactor are connected in series and a variable control unit, and the variable control unit controls the temperature of each reactor and the amount of alcohol injected into each reactor such that Formulas 1) and 2) are satisfied, and N is an integer of 2 or greater:

$$T_{n1-1} \leq T_{n1} \tag{1}$$

$$E_{n2-1} \geq E_{n2} \geq E_1 \tag{2}$$

wherein, in Formulas 1) and 2), n1 is an integer of 2 to N, and n2 is an integer of 3 to N,
$T_x$=Temperature of an x-th reactor
$E_x$={(Number of moles of alcohol injected into an x-th reactor−c*Number of moles of polycarboxylic acid injected into an x-th reactor/c*Number of moles of polycarboxylic acid injected into the first reactor) *100%}
wherein, in $T_x$ and $E_x$, x is an integer of 1 to N, and c is the number of carboxylic acid groups contained in one molecule of the polycarboxylic acid.

4. The system of claim 1, wherein the reaction unit comprises N number of reactors in which a first reactor to an N-th reactor are connected in parallel and a supply control unit, and the supply control unit controls the injection amount and the injection path of the reaction mixture injected from the mixing unit into the reaction unit such that the formation of the first unpurified product mixture in each reactor is performed semi-continuously across the N number of reactors, and N is an integer of 2 or greater.

5. The system of claim 1, wherein the neutralization unit comprises a neutralizer, and an inner space of the neutralizer is provided with one or more partition walls such that the inner space is divided into a neutralization space and a layer separation space in the left and right directions respectively and a passage connecting the two spaces is formed, and the passage starts from an upper portion of the neutralization space.

6. The system of claim 1, further comprising a filtering unit for removing solid impurities remaining in at least one of the reaction mixture, the first unpurified product mixture, the second unpurified product mixture, the organic layer stream, the ester-rich stream, and the product stream.

7. The system of claim 1, wherein the system is continuously operated.

8. The system of claim 1, wherein the polycarboxylic acid is one or more selected from the group consisting of a dicarboxylic acid, a tricarboxylic acid, and a tetracarboxylic acid.

9. The system of claim 8, wherein
the dicarboxylic acid is one or more selected from the group consisting of a linear dicarboxylic acid having 2 to 10 carbon atoms, a terephthalic acid, a phthalic acid, an isophthalic acid, a cyclohexane dicarboxylic acid, an anhydride thereof, and a derivative thereof,
the tricarboxylic acid is one or more selected from the group consisting of a citric acid, a trimellitate acid, a cyclohexane tricarboxylic acid, an anhydride thereof, and a derivative thereof, and
the tetracarboxylic acid is one or more selected from the group consisting of a benzenetetracarboxylic acid, a furantetracarboxylic acid, a cyclohexane tetracarboxylic acid, a tetrahydrofuran tetracarboxylic acid, an anhydride thereof, and a derivative thereof.

* * * * *